United States Patent [19]

Degani et al.

[11] Patent Number: 4,868,322

[45] Date of Patent: Sep. 19, 1989

[54] PROCESS FOR PREPARING TRITHIOCARBONIC ACID DIESTERS

[75] Inventors: Iacopo Degani; Rita Fochi; Valeria Regondi, all of Turin, Italy

[73] Assignee: Consiglio Nazionale Delle Ricerche, Rome, Italy

[21] Appl. No.: 212,135

[22] Filed: Jun. 28, 1988

Related U.S. Application Data

[63] Continuation of Ser. No. 505,960, Jun. 20, 1983, abandoned.

[30] Foreign Application Priority Data

Jun. 23, 1982 [IT] Italy .............................. 22010 A/82

[51] Int. Cl.$^4$ ................. C07C 153/00; C07D 277/62; C07D 277/60
[52] U.S. Cl. ................................... 558/243; 548/170; 548/152
[58] Field of Search ................. 558/243; 548/170, 152

[56] References Cited

U.S. PATENT DOCUMENTS

4,341,715  7/1982  Parlman et al. ................. 260/455 B

FOREIGN PATENT DOCUMENTS

1468651  3/1969  Fed. Rep. of Germany ... 260/455 B

OTHER PUBLICATIONS

Chemical Abstracts, vol. 89, No. 25, Dec. 18, 1978, p. 563, No. 215082b, Columbus, Ohio, U.S.A.

Kirk-Othmer, *Encyclopedia of Chemical Technology*, 1979, 5, pp. 62-68.
Dehmlow et al., (Dehmlow), *Phase Transfer Catalysis* (Deerfield Beach, Fla., Verlag Chemie, 1980), p. 76.
Reid, Organic Chemistry of Bivalent Sulfur, vol. IV, Chem. Publishing Co., Inc., New York, 1962.
Smith, Catalysis in Organic Synthesis, Academic Press, Inc., New York, 1977, (Contribution by Regen).
"The Synthesis of Organic Trithiocarbonates", Godt and Wann, Journal of the American Chemical Society, Oct. 1961, vol. 26, pp. 2047-2051.

*Primary Examiner*—Mary C. Lee
*Assistant Examiner*—Robert C. Whittenbaugh
*Attorney, Agent, or Firm*—Stevens, Davis, Miller & Mosher

[57] ABSTRACT

A new process is described for the preparation of trithiocarbonic acid esters of formula:

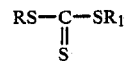

in which R and $R_1$, which can be the same or different, are aliphatic, alicyclic, aromatic or heterocyclic radicals. The new process is characterized in that an organic hydrosulphide and a base, or an inorganic sulphide, are reacted with carbon disulphide and an organic halide in stoichiometric proportions in the absence of organic solvents, in the presence of an aqueous phase and a phase transfer catalyst.

5 Claims, No Drawings

PROCESS FOR PREPARING TRITHIOCARBONIC ACID DIESTERS

This application is a continuation of application SERIAL NO. 505,960, filed JUNE 20, 1983 now abandoned.

This invention relates to a new process for producing trithiocarbonic acid derivatives.

More precisely, the present invention relates to a process for producing trithiocarbonic diesters of formula:

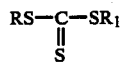

in which R and $R_1$, which can be the same or different, are aliphatic, alicyclic, aromatic or heterocyclic radicals.

Many compounds of formula (I) are already known in the literature and have been used in various technological fields. The most important uses are in the field of pesticides and petroleum product additives.

Because of the practical importance of these compounds, various methods have been proposed for their preparation (J. Am. Chem. Soc. October 1961, 4047–4051).

Ignoring the more specific methods valid only for particular compounds, the known syntheses most widely used are represented by the following reaction schemes:

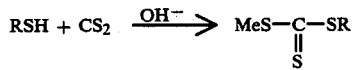 (A)

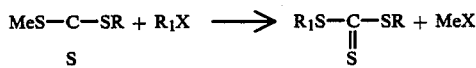

in which R and $R_1$ are equal or different organic radicals, X is halogen and Me is alkaline metal (B)

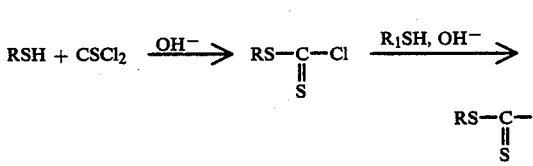

in which R and $R_1$ are equal or different organic radicals.

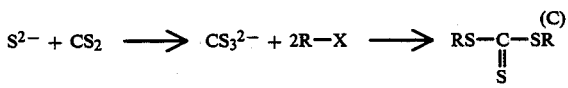 (C)

in which R is an organic radical and X is halogen.

These methods are not generally suitable for large-scale production, both because they require the use and thus the recovery of considerable quantities of solvents, and because they generally require long reaction times and complicated methods of separating and recovering both the intermediates and the final products, with relatively low yields.

From the ecological viewpoint, said processes are also hardly convenient in that they give rise to very polluting effluents.

We have now discovered the subject matter of the present invention, namely a process which can be used on an industrial scale for the production of any symmetrical or asymmetrical ester of trithiocarbonic acid, in an economically convenient manner.

The process claimed by us can be represented by the following reaction scheme of general character:

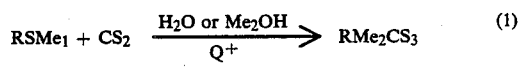 (1)

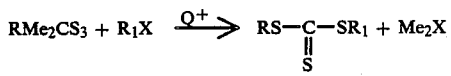

in which:
R is an aliphatic, alicyclic, aromatic or heterocyclic radical, or $Me_1$;
$R_1$, which can be the same as or different from R, is an aliphatic, alicyclic, aromatic or heterocyclic radical;
$Me_1$ is Na, K or H;
$Me_2$, which can be the same as or different from $Me_1$, is Na or K;
X is Cl, Br or I.

The process is characterised by being carried out without separating intermediate products, in the presence of an aqueous phase and a phase transfer catalyst chosen from the group consisting of quaternary ammonium and phosphonium salts.

If the preparation of symmetrical esters and asymmetrical esters is considered separately, the equations (1) which represent the processes according to the present invention can be more specifically indicated as follows:

For the preparation of symmetrical trithiocarbonic acid esters:

 (2)

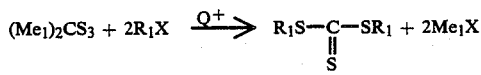

in which
$Me_1$ is Na or K;
$R_1$ is an aliphatic, alicyclic, aromatic or heterocyclic radical;
X is Cl, Br or I.

The reaction is carried out using the reagents in stoichiometric quantity, in the absence of organic solvents but with the addition of a small quantity of water, at a temperature between 15° and 100° C. according to the products treated. The inorganic sulphide and the carbon disulphide are initially reacted with the phase transfer catalyst and water under energetic agitation at ambient temperature.

The organic halide is added later, and the mixture heated until the reaction is complete, this being indicated by the disappearance of any coloration of the aqueous phase. The reaction time varies within a wide range, but is generally short.

The trithiocarbonate is separated from the cooled reaction mixture either by simple decantation followed by washing the organic phase with water or hydroalcoholic solutions if the catalyst is sufficiently soluble in water or hydroalcoholic solutions, or by extraction with a suitable organic solvent followed by filtration of the extract through silica gel in order to eliminate the catalyst, if this is essentially soluble in the organic phase.

Yields are always very high.

For the preparation of asymmetrical trithiocarbonic acid esters:

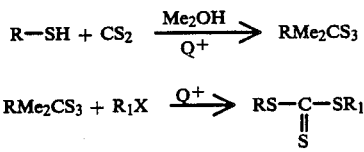

in which:

Me$_2$ is Na or K:

R is an aliphatic, alicyclic, aromatic or heterocyclic radical;

R$_1$, which can be the same as or different from R, is an aliphatic, alicyclic, aromatic or heterocyclic radical;

X is Cl, Br or I.

The reaction is carried out using the reagents in stoichiometric quantity in the absence of solvents, but in the presence of an aqueous alkaline hydrate at a temperature of between 15° and 100° C., according to the products treated.

Again, the mercaptan, the carbon disulphide, the alkaline base and the phase transfer catalyst are initially reacted under agitation, whereas the alkyl halide is added later and the reaction is continued until complete. Generally, the end of the reaction is indicated by the disappearance of the aqueous phase coloration.

In all cases, the phase transfer catalyst, which is the determining element of the process, is chosen from the group consisting of: $(C_8H_{17})_4N^+Br^-$, $C_{16}H_{33}(C_4H_9)_3N^+Br^-$, $(C_8H_{17})_3CH_3N^+Cl^-$, $(C_4H_9)_4N^+Br^-$, $PhCH_2(C_3H_7)_3N^+Br^-$, $C_{16}H_{33}(C_3H_7)_3N^+Br^-$, $C_{16}H_{33}(C_4H_9)_3P^+Br^-$, $(C_4H_9)_4P^+Br^-$ and their mixtures.

The catalysts are used in the proportion of 1–15 g per mole of alkyl halide.

The water and/or aqueous alkaline base are added to the system in a quantity of 250–350 cc per mole of carbon disulphide.

A certain number of practical examples of the process are given hereinafter by way of non-limiting example.

In all cases the process was carried out without separating intermediate products and without using solvents, at moderate temperature and with short reaction times, and giving rise to only small quantities of effluent water. The yields were very high in all cases.

It is thus evidently a process of general application, highly significant from an industrial viewpoint, and very convenient compared with the known processes from many aspects.

EXAMPLE 1

Preparation of Dioctyl Trithiocarbonate

A mixture formed from 0.1 moles of Na$_2$S.9H$_2$O, 0.1 moles of carbon disulphide, 0.2 g of Aliquat 336 and 30 cc of water is agitated energetically at ambient temperature (18°–20° C.) for 19 minutes. 0.2 moles of octyl bromide are added to the solution obtained, which is of an intensely red colour. The temperature is then slowly raised from 20° to 70° over about 15–20 minutes, and, still under energetic agitation, this temperature is maintained until decoloration of the aqueous solution. The reaction, which is followed by G.C. (conditions: SE 30, 5% on Varaport 30; temperature programmed from 100° to 250°), is complete in 90 minutes. The mixture is cooled, extracted with petroleum ether and filtered through silica gel (eluent: petroleum ether) in order to eliminate the catalyst. The solvent is evaporated under vacuum, and 32.73 g of pure dioctyl trithiocarbonate (G.C., N.M.R.) are obtained with a yield of 98%.

The effluent water contains only minimum quantities of polluting by-products.

The same process was repeated for comparison purposes in an identical manner, but with the absence of the phase transfer catalyst.

5–6 hours of agitation at ambient temperature (20° C.) and 40 hours of heating to 70° C. were necessary for completing the reaction.

On termination of the reaction, chromatographic analysis of the crude product gave the following values:

| | |
|---|---|
| octyl mercaptan | 7% |
| octyl bromide | 28% |
| dioctyl disulphide | 7% |
| dioctyl trithiocarbonate | 41% |

Further symmetrical trithiocarbonates were prepared by exactly following the method described in Example 1. The essential data of the process are collected in Table 1 below, in which:

A is $(C_8H_{17})_3CH_3N^+Cl^-$ (Aliquat 336)

B is $(C_4H_9)_4N^+Br^-$

C is $C_{16}H_{33}(C_4H_9)_3P^+Br^-$.

The catalyst quantity always relates to the reaction carried out with 0.2 moles of halide, 0.1 moles of sodium sulphide and 0.1 moles of CS$_2$.

TABLE 1

Symmetrical trithiocarbonates

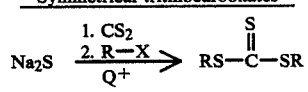

| R | X | Catalyst (g) | Reaction time at 70° C. (hours) | Yield % | B.P. °C./mm Hg or M.P °C. |
|---|---|---|---|---|---|
| i-C$_3$H$_7$ | Br | A(1) | 2 | 90 | 75/0.3 |
| i-C$_3$H$_7$ | I | C(1) | 4 | 91 | 75/0.3 |
| n-C$_4$H$_9$ | Br | A(0.2) | 1 | 90 | 131/0.5 |
| C$_3$H$_7$—CH<br>\|<br>CH$_3$ | Br | A(1) | 6 | 90 | 130/0.5 |

TABLE 1-continued

Symmetrical trithiocarbonates $$Na_2S \xrightarrow[Q^+]{\begin{array}{c}1.\ CS_2\\ 2.\ R-X\end{array}} RS\overset{\overset{\displaystyle S}{\|}}{-}C-SR$$

| R | X | Catalyst (g) | Reaction time at 70° C. (hours) | Yield % | B.P. °C./mm Hg or M.P °C. |
|---|---|---|---|---|---|
| $C_3H_7-\underset{\underset{\displaystyle CH_3}{\|}}{CH}$ | Br | B(1) | 6 | 90 | 130/0.5 |
| $C_3H_7-\underset{\underset{\displaystyle CH_3}{\|}}{CH}$ | Br | C(1) | 2 | 94 | 130/0.5 |
| Cyclopentyl | Br | A(0.2) | 3 | 95 | 165/0.6 |
| Cyclopentyl | Br | C(1) | 1 | 90 | 165/0.6 |
| $n\text{-}C_8H_{17}$ | Cl | A(1) | 7 | 92 | 190–193/0.3 |
| $n\text{-}C_8H_{17}$ | Cl | B(1) | 7 | 90 | 190–193/0.3 |
| $n\text{-}C_8H_{17}$ | Cl | C(1) | 5 | 96 | 190–193/0.3 |
| $n\text{-}C_8H_{17}$ | Br | A(0.2) | 1.5 | quant. | 190–193/0.3 |
| $n\text{-}C_8H_{17}$ | Br | B(1) | 3 | 97 | 190–193/0.3 |
| $n\text{-}C_8H_{17}$ | I | A(1) | 8 | 90 | 190–193/0.3 |
| $C_6H_{13}-\underset{\underset{\displaystyle CH_3}{\|}}{CH}$ | I | C(1) | 14 | 80 | 167/0.3 |
| $n\text{-}C_{12}H_{25}$ | Br | A(0.2) | 1.5 | 97 | 54 |
| $n\text{-}C_{18}H_{37}$ | Br | A(0.2) | 3 | quant. | 54 |
| $C_6H_5-CH_2$ | Cl | A(0.2) | 1 | 91 | 210/0.3 |
| $4\text{-}Cl-C_6H_4-CH_2$ | Cl | A(0.2) | 0.25 | 98 | 75 |
| $4\text{-}t\text{-}C_4H_9-C_6H_4-CH_2$ | Br | A(0.2) | 0.5 | quant. | |
| $-CH_2-CH_2-$ | Cl | A(0.2) | 1.5 | 93 | 36 |
| $CH_2=CH-CH_2$ | Cl | A(0.2) | 2(a.t.) | 90 | 100/0.3 |
| $CH_2=CH-CH_2$ | Br | A(0.2) | 0.25 | 90 | 100/0.3 |

EXAMPLE 2

Preparation of Butyl Octyl Trithiocarbonate 0.1 moles of carbon disulphide and 0.2 g of Aliquat 336 are added to a solution of 0.1 moles of butyl mercaptan in 31 cc of 20% KOH. The mixture is agitated energetically at ambient temperature for 15 minutes.

0.1 moles of octyl bromide are added to the solution obtained, which is of an intense orange colour.

The temperature is then slowly raised from 20° to 70° over 15–20 minutes, and this temperature is maintained, still under energetic agitation, until decoloration of the aqueous solution. The reaction, which is followed by means of G.C. (conditions: SE 30, 5% on Varaport 30; temperature programmed from 100° to 250°) is complete in 30 minutes. The mixture is cooled, extracted with petroleum ether and filtered through silica gel (eluent: petroleum ether) in order to eliminate the catalyst. The solvent is evaporated under vacuum to give 26.4 g of pure butyl octyl trithiocarbonate (G.C., N.M.R.) with a yield of 95%.

The effluent water contains only a minimum quantity of pollutant impurities.

Numerous asymmetrical trithiocarbonates were prepared following the operational method described in Example 2. The essential data of the processes carried out are given in Table 2 below, where the symbols A, B, C have the same meanings as heretofore.

In this case, the catalyst quantity relates to the reaction carried out with 0.1 moles of mercaptan, 0.1 moles of halide and 0.1 moles of carbon disulphide.

TABLE 2

Asymmetrical trithiocarbonates $$R-SH \xrightarrow[Q^+]{\begin{array}{c}1.\ KOH,\ CS_2\\ 2.\ R'-X\end{array}} RS\overset{\overset{\displaystyle S}{\|}}{-}C-SR'$$

| R | R' | X | Catalyst (g) | Reaction time at 70° C. (min) | Yield % | B.P. °C./mm Hg or M.P. °C. |
|---|---|---|---|---|---|---|
| $i\text{-}C_3H_7$ | $n\text{-}C_8H_{17}$ | Br | A(0.2) | 15 | quant. | 142–0.3 |
| $i\text{-}C_3H_7$ | $n\text{-}C_8H_{17}$ | Br | B(0.2) | 30 | 95 | 142–144/0.3 |
| $n\text{-}C_4H_9$ | $n\text{-}C_4H_9$ | Br | A(0.2) | 15 | 95 | 131/0.5 |
| $n\text{-}C_4H_9$ | Cyclopentyl | Br | A(0.2) | 90 | 90 | 138–139/0.3 |
| $n\text{-}C_4H_9$ | $C_3H_7-\underset{\underset{\displaystyle CH_3}{\|}}{CH}$ | Br | A(1) | 2 hours | 94 | 117/0.3 |
| $n\text{-}C_4H_9$ | $C_3H_7-\underset{\underset{\displaystyle CH_3}{\|}}{CH}$ | Br | C(1) | 2 hours | 93 | 117/0.3 |

TABLE 2-continued

Asymmetrical trithiocarbonates $$R-SH \xrightarrow[\underset{Q^+}{2.\ R'-X}]{1.\ KOH,\ CS_2} RS-\overset{\overset{S}{\|}}{C}-SR'$$

| R | R' | X | Catalyst (g) | Reaction time at 70° C. (min) | Yield % | B.P. °C./mm Hg or M.P. °C. |
|---|---|---|---|---|---|---|
| n-C$_4$H$_9$ | n-C$_8$H$_{17}$ | Cl | A(1) | 7 hours | 80 | 173–174/0.4 |
| n-C$_4$H$_9$ | n-C$_8$H$_{17}$ | Cl | B(1) | 5 hours | 87 | 173–174/0.4 |
| n-C$_4$H$_9$ | n-C$_8$H$_{17}$ | Cl | C(1) | 8 hours | 81 | 173–174/0.4 |
| n-C$_4$H$_9$ | n-C$_8$H$_{17}$ | Br | A(0.2) | 15 | 98 | 173–174/0.4 |
| n-C$_4$H$_9$ | n-C$_8$H$_{17}$ | Br | B(0.2) | 30 | 96 | 173–174/0.4 |
| n-C$_4$H$_9$ | n-C$_8$H$_{17}$ | I | A(0.2) | 5 | quant. | 173–174/0.4 |
| n-C$_4$H$_9$ | n-C$_8$H$_{17}$ | I | B(0.2) | 30 | 94 | |
| n-C$_4$H$_9$ | n-C$_8$H$_{17}$ | I | B(0.2) | 15 | quant. | 173–174/0.4 |
| n-C$_4$H$_9$ | 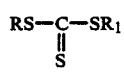 C$_6$H$_{13}$—CH(CH$_3$) | Br | A(1) | 5 hours | 90 | 154–155/0.4 |
| n-C$_4$H$_9$ | C$_6$H$_{13}$—CH(CH$_3$) | I | A(1) | 20 | quant. | 154–155/0.4 |
| n-C$_4$H$_9$ | n-C$_{12}$H$_{25}$ | Cl | A(1) | 10 hours | 89 | 196/0.3 |
| n-C$_4$H$_9$ | n-C$_{12}$H$_{25}$ | Cl | B(1) | 10 hours | 86 | 196/0.3 |
| n-C$_4$H$_9$ | n-C$_{12}$H$_{25}$ | Cl | C(1) | 8 hours | 90 | 196/0.3 |
| n-C$_4$H$_9$ | n-C$_{16}$H$_{33}$ | Br | A(0.2) | 30 | quant. | 42 |
| n-C$_4$H$_9$ | C$_6$H$_5$—CH$_2$ | Cl | A(0.2) | 15 | quant. | 156/0.3 |
| t-C$_4$H$_9$ | n-C$_4$H$_9$ | Br | A(0.2) | 15 | 92 | 100/0.3 |
| t-C$_4$H$_9$ | n-C$_8$H$_{17}$ | Br | A(0.2) | 15 | 96 | 157–160/0.4 |
| t-C$_4$H$_9$ | n-C$_{16}$H$_{33}$ | Br | A(0.2) | 15 | 95 | 51 |
| t-C$_4$H$_9$ | C$_6$H$_5$—CH$_2$ | Cl | A(0.2) | 15 | 97 | 155/0.3 |
| n-C$_8$H$_{17}$ | n-C$_4$H$_9$ | Br | A(0.2) | 15 | 98 | 173–174/0.4 |
| n-C$_8$H$_{17}$ | n-C$_8$H$_{17}$ | Br | A(0.2) | 15 | quant. | 190–193/0.3 |
| n-C$_8$H$_{17}$ | C$_6$H$_5$—CH$_2$ | Cl | A(0.2) | 15 | quant. | 188/0.3 |
| n-C$_{12}$H$_{25}$ | i-C$_3$H$_7$ | Br | A(1) | 3 hours | 97 | 180/0.3 |
| n-C$_{12}$H$_{25}$ | CH$_2$=CH—CH$_2$ | Cl | A(0.2) | 1.5 hours (a.t.) | 94 | 190/0.3 |
| n-C$_{12}$H$_{25}$ | CH$_2$=CH—CH$_2$ | Br | A(0.2) | 30 (a.t.) | quant. | 190/0.3 |
| n-C$_{16}$H$_{33}$ | n-C$_4$H$_9$ | Br | A(0.2) | 15 | 98 | 42 |
| n-C$_{16}$H$_{33}$ | C$_6$H$_5$—CH$_2$ | Cl | A(0.2) | 15 | quant. | 54 |
| C$_6$H$_5$—CH$_2$ | n-C$_4$H$_9$ | Br | A(0.2) | 15 | 98 | 158/0.3 |
| C$_6$H$_5$—CH$_2$ | n-C$_8$H$_{17}$ | Br | A(0.2) | 15 | quant. | 188/0.3 |
| C$_6$H$_5$ | n-C$_4$H$_9$ | Br | C(1) | 15 | 50 | 140/0.3 |
| 2-Benzothiazolyl | n-C$_4$H$_9$ | Br | C(1) | 15 | 50 | 125–126/0.3 |

As initially stated, the products prepared according to the new process can be used in the pesticide field as intermediates or final products, in the mineral additive field, and in the different known fields of the literature.

We claim:

1. A process for producing trithiocarbonic acid diesters of formula $$RS-\overset{\overset{S}{\|}}{C}-SR_1$$

in which R and R$_1$, which can be the same or different, are aliphatic, alicyclic, aromatic or heterocyclic radicals, comprising reacting an organic hydrosulphide RSMe where R has the meaning above recited, and Me is H or Na or K, or an inorganic sulphide Me$'_2$S wherein Me' is Na or K, with carbon disulphide and an alkylhalide R$_1$X wherein X=halogen and R$_1$ has the above meaning, in the presence of an alkaline or neutral aqueous phase, characterized in that the reaction is carried out in the presence of a phase transfer catalyst selected from the group consisting of (C$_8$H$_{17}$)$_4$N$^+$Br$^-$, C$_{16}$H$_{33}$(C$_4$H$_9$)$_3$N$^+$Br$^-$, (C$_8$H$_{17}$)$_3$CH$_3$N$^+$Cl$^-$, (C$_4$H$_9$)$_4$N$^+$Br$^-$, PhCH$_2$(C$_3$H$_7$)$_3$N$^+$Br$^-$, C$_{16}$H$_{33}$(C$_3$H$_7$)$_3$N$^+$Br$^-$, C$_{16}$H$_{33}$(C$_4$H$_9$)$_3$P$^+$Br$^-$, (C$_4$H$_9$)$_4$P$^+$Br$^-$ and mixtures thereof.

2. A process according to claim 1 for producing symmetrical diesters in which R is equal to R$_1$, characterized in that Na or K sulphide is reacted with carbon disulphide and an alkyl halide RX.

3. A process as claimed in claim 1, wherein the reagents are used in stoichiometric proportions.

4. A process as claimed in claim 1, carried out at a temperature of between 15° and 100° C.

5. A process as claimed in claim 1, wherein the catalyst is used in the proportion of 1–15 g per mole of alkyl halide.